United States Patent [19]
Frantzen et al.

[11] Patent Number: 5,948,184
[45] Date of Patent: Sep. 7, 1999

[54] FLEXIBLE HOUSING FOR INTRACORPOREAL USE

[75] Inventors: John J. Frantzen, Copperopolis, Calif.; Sepehr Fariabi, Topaz, Conn.

[73] Assignee: Devices for Vascular Intervention, Inc., Santa Clara, Calif.

[21] Appl. No.: 08/924,408

[22] Filed: Aug. 22, 1997

Related U.S. Application Data

[60] Continuation of application No. 08/589,969, Jan. 23, 1996, abandoned, which is a division of application No. 08/088,930, Jul. 7, 1993, Pat. No. 5,514,115.

[51] Int. Cl.⁶ ..................................................... C22F 1/10
[52] U.S. Cl. ........................ 148/563; 148/402; 148/670
[58] Field of Search ................................. 148/402, 563, 148/670, 676

[56] References Cited

U.S. PATENT DOCUMENTS

| | | | |
|---|---|---|---|
| Re. 33,569 | 4/1991 | Gifford, III et al. | 606/159 |
| 3,890,977 | 6/1975 | Wilson | 128/418 |
| 4,484,955 | 11/1984 | Hochstrin | 148/402 |
| 4,505,767 | 3/1985 | Quin | 148/402 |
| 4,533,411 | 8/1985 | Melton | 148/563 |
| 4,665,906 | 5/1987 | Jervis | 128/92 YN |
| 4,758,285 | 7/1988 | Hodgson et al. | 148/563 |
| 4,771,774 | 9/1988 | Simpson et al. | 128/305 |
| 4,799,474 | 1/1989 | Ueda | 128/4 |
| 4,881,981 | 11/1989 | Thoma et al. | 148/11.5 R |
| 4,919,133 | 4/1990 | Chiang | 606/159 |
| 4,930,494 | 6/1990 | Takehana et al. | 128/4 |
| 4,969,890 | 11/1990 | Sugita et al. | 606/192 |
| 4,979,951 | 12/1990 | Simpson | 606/159 |
| 5,019,040 | 5/1991 | Itaoka | 604/95 |
| 5,025,799 | 6/1991 | Wilson | 128/772 |
| 5,067,957 | 11/1991 | Jervis | 606/108 |
| 5,069,226 | 12/1991 | Yamauchi et al. | 128/772 |
| 5,078,722 | 1/1992 | Stevens | 606/159 |
| 5,085,662 | 2/1992 | Willard | 606/159 |
| 5,089,005 | 2/1992 | Harada | 606/194 |
| 5,092,873 | 3/1992 | Simpson et al. | 606/159 |
| 5,120,308 | 6/1992 | Hess | 604/95 |
| 5,135,517 | 8/1992 | McCoy | 604/281 |
| 5,147,370 | 9/1992 | McNamara et al. | 606/108 |
| 5,154,705 | 10/1992 | Fleischhacker et al. | 604/282 |
| 5,171,233 | 12/1992 | Amplatz et al. | 604/281 |
| 5,181,920 | 1/1993 | Mueller et al. | 606/159 |
| 5,243,996 | 9/1993 | Hall | 128/772 |
| 5,334,168 | 8/1994 | Hemmer | 604/281 |
| 5,368,049 | 11/1994 | Raman et al. | 128/772 |

FOREIGN PATENT DOCUMENTS

| | | | |
|---|---|---|---|
| 0 145 166 | 6/1985 | European Pat. Off. | |
| 44047 | of 1983 | Japan . | |
| 50951 | of 1983 | Japan . | |
| 62-284047 | 12/1987 | Japan | 148/563 |
| 1-242763 | 9/1989 | Japan | 148/563 |
| 1 600 000 | 10/1981 | United Kingdom . | |

OTHER PUBLICATIONS

R. J. Wasilewski, "The Effects of Applied Stress on the Martensitic Transformation in TiNi".
C. M. Jackson et al., "55–Nitinol—The Alloy With a Memory: Its Physical Metallurgy, Properties, and Applications," *NASA*, 1972.
H. J. Wagner, "What you can do with that 'memory' alloy, "*Metals*, 1969.
Wayman, "Some Applications of Shape Memory Alloys," *Journal of Metals*, 1980.

*Primary Examiner*—George Wyszomierski
*Attorney, Agent, or Firm*—Heller, Ehrman, White & McAuliffe

[57] ABSTRACT

An elongated flexible housing for an atherectomy or other intracorporeal catheter which is formed of a shape memory alloy such as an alloy formed predominantly of NiTi intermetallic compound. The housing preferably has an inner chamber with a tissue cutter or other diagnostic or therapeutic system provided within the chamber to sever stenotic material which is urged into the chamber through a opening or window in the housing. In one embodiment the housing has at least one section which is relatively flexible with adjacent sections which are relatively stiff to provide an increase in the overall flexibility of the housing.

7 Claims, 3 Drawing Sheets

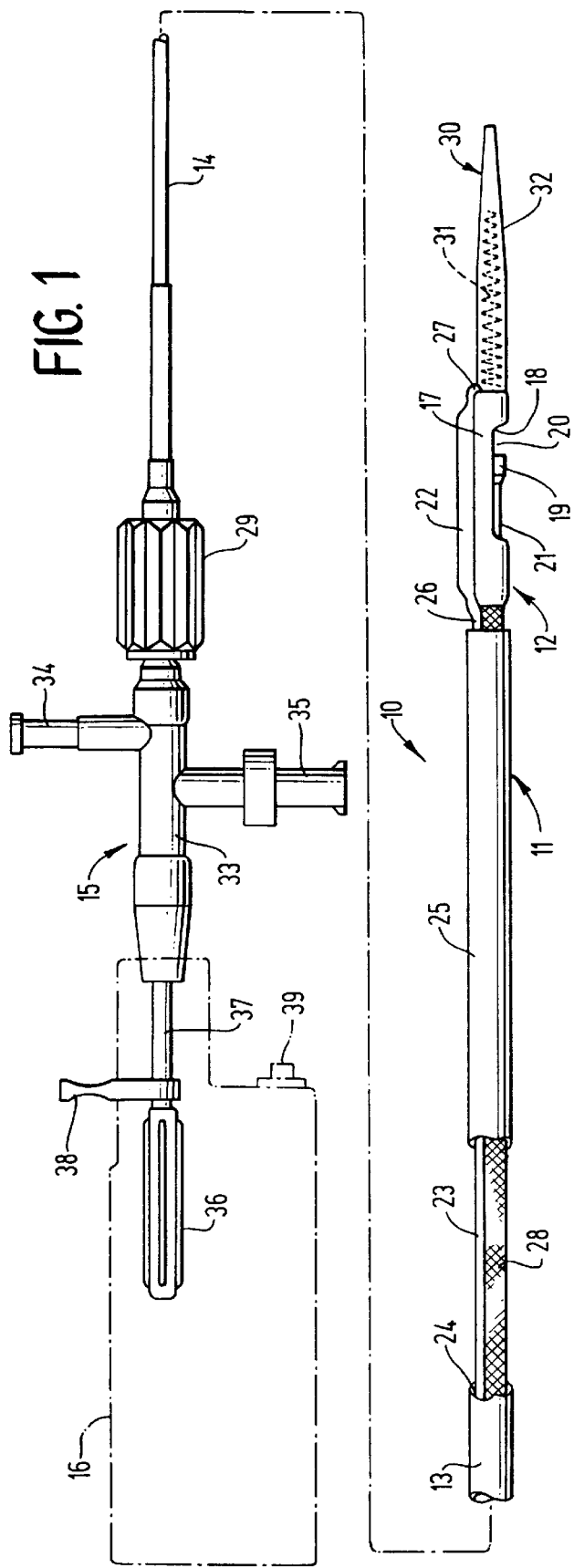
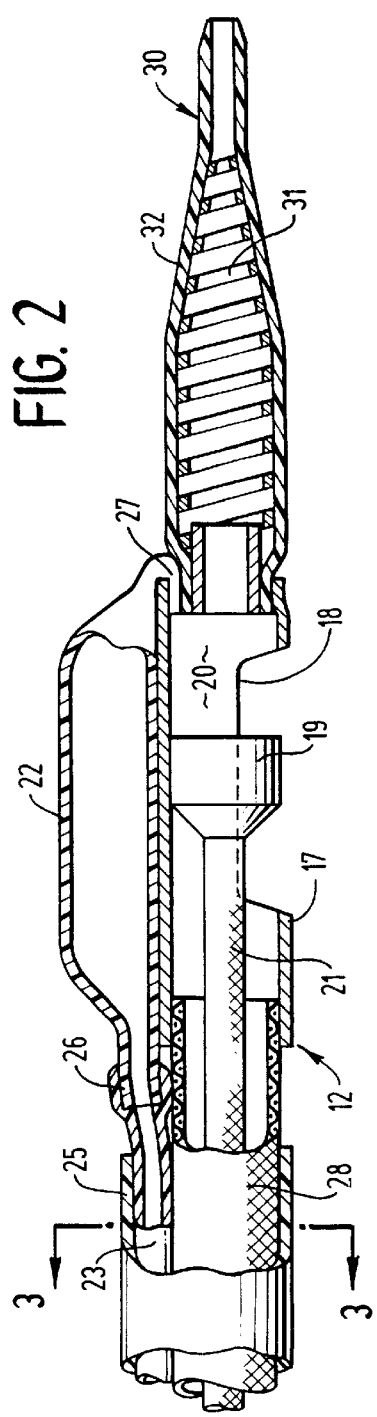
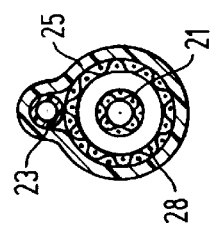

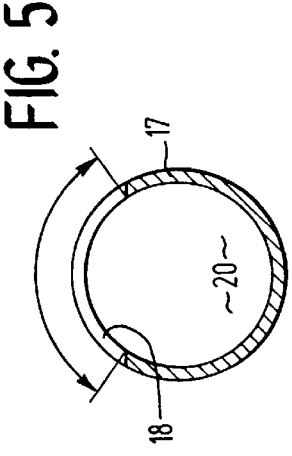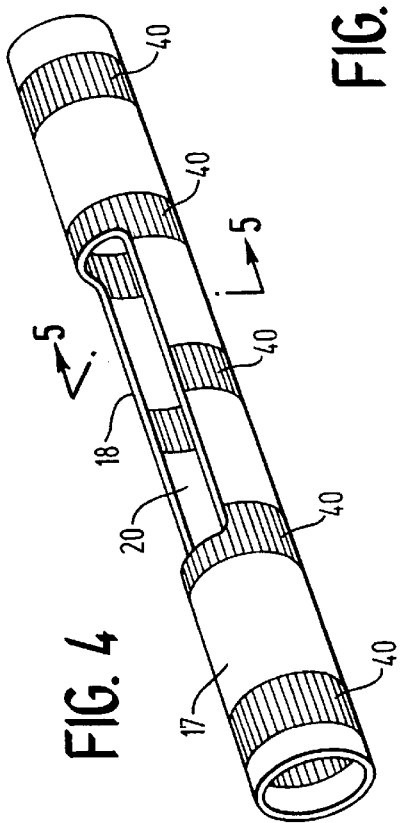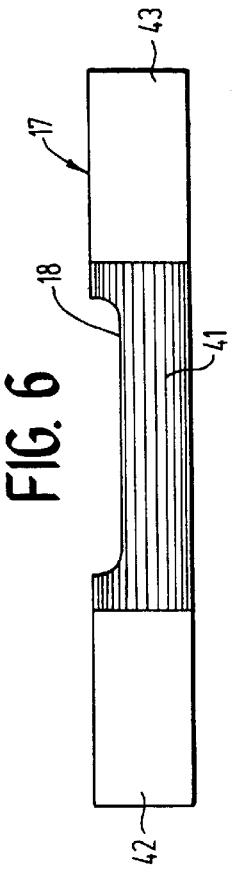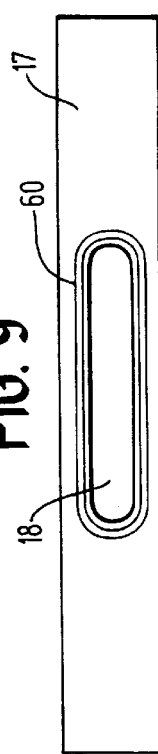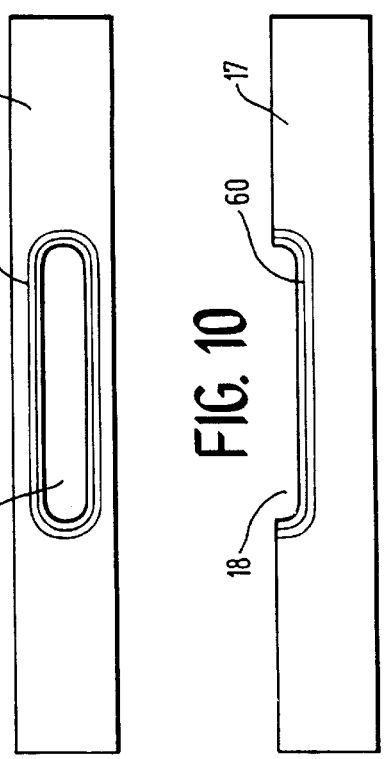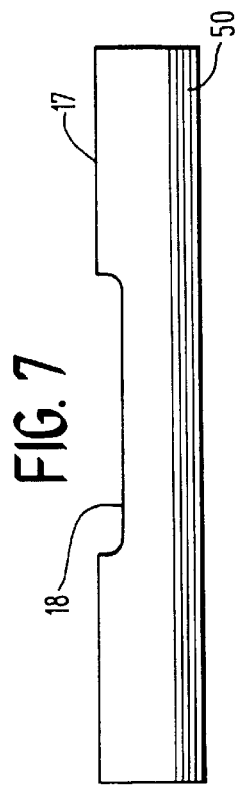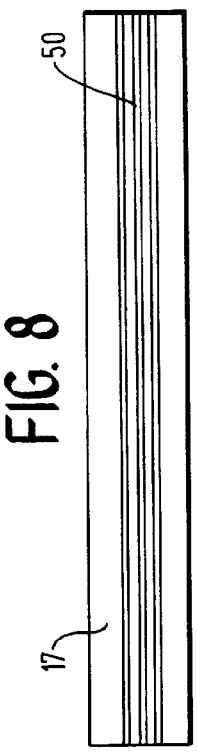

FLEXIBLE HOUSING FOR INTRACORPOREAL USE

This is a continuation of application Ser. No. 08/589,969 filed on Jan. 23, 1996 now abandoned, which is a divisional of Ser. No. 08/088,930 filed Jul. 7, 1993, now U.S. Pat. No. 5,514,115.

BACKGROUND OF THE INVENTION

This invention generally relates to a housing or other hollow device for intracorporeal use such as performing a therapeutic or diagnostic procedure within a body lumen or cavity within the housing. The housing is particularly useful with a catheter for removing tissue from a body lumen or cavity, such as the removal of atheroma from a patient's artery in an atherectomy procedure.

In typical coronary atherectomy procedures, a guiding catheter having a preshaped distal tip is percutaneously introduced into a patient's cardiovascular system through the femoral artery and advanced therein until the preshaped distal tip of the guiding catheter is disposed within the ascending aorta adjacent the ostium of the coronary artery in which the procedure is to be performed. The guiding catheter is twisted or torqued from the proximal end, which is outside the patient, to turn the distal tip of the guiding catheter so that it can be guided into the desired coronary ostium. An atherectomy catheter having a cutter head on its distal end is introduced into and advanced through the guiding catheter and out the distal tip thereof until the cutter head is properly positioned across the lesion to be treated. Once properly positioned, a positioning balloon on one side of the cutter head is inflated with liquid at relatively high pressures (e.g., 3–6 atmospheres) to press the cutter head against the stenotic tissue to be removed so that such tissue will be urged into the interior chamber of the cutter head where a cutting blade severs the tissue from the artery wall. The positioning balloon is then deflated so that the atherectomy catheter can be repositioned, e.g. rotated, to remove additional tissue from the stenosis in essentially the same manner. When the procedure is completed, the positioning balloon is finally deflated and the catheter removed from the artery so that blood flow can resume through the artery. In commercially available atherectomy catheters such as the Simpson Atherocath®, which is available from the assignee of the present application. Devices for Vascular Intervention (DVI), the cutter blade is axially rotated a relatively high speeds, e.g. 2000 rpm while the blade is advanced from one. end of the housing to the other in order to sever the stenotic tissue which is urged into the interior chamber.

Reference is made to U.S. Reissue Pat. No. 33,569 (Gifford, III et al.), U.S. Pat. No. 4,771,774 (Simpson et al.), and U.S. Pat. No. 5,092,873 (Simpson et al.) which describe further details of atherectomy catheters and which are incorporated herein in their entirety by reference.

The cutter housing on most atherectomy catheters have been formed of high strength materials such as stainless steel. As a result, they have been rather stiff and this stiffness has been found to significantly restrict the ability of the atherectomy catheter to be advanced through tortuous arterial anatomy and to limit how far an atherectomy catheter can be advanced within a patient's arterial system. Softer, more flexible materials might be employed to form the cutter housing but when the housing is made of softer, more flexible materials, the housing can deform, e.g. kink, when being advanced through the shaped distal end of the guiding catheter or tortuous arterial anatomy so that the cutting blade within the housing cannot be properly moved within the inner chamber of the cutter housing for effective tissue removal. It has also been found that, if the housing is too soft or becomes deformed in the procedure, the cutting blade frequently will not remain within the inner chamber of the cutter housing as it is advanced through the inner chamber to sever tissue, thereby preventing the completion of the procedure. Moreover, in the latter instance the excursion of a rotating cutting blade through a side opening or window in the cutter housing can cause serious damage to the arterial wall. If the cutting blade cannot be withdrawn back into the inner chamber of the cutter housing through the window, there can be difficulties in withdrawing the atherectomy catheter back into the guiding catheter, requiring the removal of both the atherectomy catheter and the guiding catheter. If both the guiding catheter and the atherectomy catheter must be removed, replacement catheters would have to be advanced through the patient's arterial system, increasing considerably the length and the cost of the atherectomy procedure.

What has been needed and has been heretofore unavailable is a relatively flexible cutter housing for an atherectomy catheter which allows for effective cutting operations, which maintains its shape and which retains the cutting blade within the inner chamber of the housing during the procedure. The present invention satisfies these and other needs.

SUMMARY OF THE INVENTION

The present invention is directed to an improved housing for intracorporeal use and particularly to a housing for a catheter adapted to remove tissue or other material from a body lumen or cavity, such as an atherectomy catheter for removal of atheroma from a patient's artery.

The flexible housing in one aspect of the invention has an inner chamber adapted to facilitate performance of a diagnostic or therapeutic procedure and is formed of a shape memory alloy which may have pseudoelastic, sometimes called superelastic, characteristics. The alloy preferably contains a predominant amount of NiTi, an intermetallic compound of nickel and titanium in a near equiatomic ratio of about 1:1, to provide improved housing flexibility yet also provide sufficient housing strength to maintain the transverse shape of an inner chamber within the housing. The preferred alloy material of nickel and titanium is frequently called NITINOL, an acronym for Nickel Titanium Naval Ordnance Laboratory where it was initially developed. A suitable alloy composition includes about 30% to about 52% titanium, about 38% to about 52% nickel and additional alloying elements in amounts totaling not more than about 20% in the case of copper and not more than about 10% in the case of other alloying elements. The additional alloying elements may be selected from the group consisting of up to 3% each of iron, cobalt, chromium, platinum palladium, zirconium, hafnium and niobium and up to about 10% vanadium. Generally, the nickel level should be at least about 38%, but at. nickel levels above 52% the alloy becomes too brittle to fabricate by cold working. Metallurgically, the alloy consists mostly of a NiTi intermetallic compound and smaller quantities of other alloy constituents. In addition to the NiTi intermetallic, when nickel is in excess, $Ni_{14}Ti_{11}$, $Ni_3Ti_2$ or $Ni_3Ti$ may be formed and when titanium is in excess, $Ti_2Ni$ may be formed. As used herein all references to percent alloy compositions are atomic percent unless otherwise noted. The composition is selected within the above described ranges along with the thermomechanical processing variables for forming the flexible housing to provide a desired final austenite transition temperature ($A_f$). For shape memory effects at or below body temperature the final austenite transformation temperature ($A_f$) should range about 30° to about 60° C. and preferably should be well above body temperature (37° C.), e.g. about 47° C. For pseudoelastic characteristics at body temperature the alloy composition and the thermomechanical processing should be chosen to provide an $A_f$ below body temperature (37° C.) and preferably below 25° C. The thermomechanical processing involves cold working the product and then thermally treating the cold worked product to generate the desired metallurgical structure. Usually, there will be a series of cold working steps with each cold working step followed by stress relieving heat treatment at a temperature between about 600° and about 800° C., typically about 675° C. for about 15 minutes, to facilitate subsequent cold working. The final cold working step should effect a size reduction of at least about 10%, preferably about 20% to about 75%, and the final heat treatment should be selected to develop the desired housing properties. Where all or part of the housing is to be in the martensite phase at body temperature, the composition should be at or near equiatomic Ni and Ti to form the binary NiTi composition, whereas, if the housing is to be in the austenite phase at body temperature, the nickel should be at or more than 50%. Significant amounts of alloying elements may be included to lower the $A_f$ to a temperature below body temperature.

If the housing is to be in a stable martensite phase at body temperature, the housing or one or more portions thereof should be heat treated after the final cold working step at a temperature between about 375° and about 600° C., preferably about 450° C. to about 475°, to impart the desired shape memory effect to the entire housing or one or more portions. thereof. If the housing is to be in a stable austenite phase at or below body temperature, the housing should be given a thermal treatment at a temperature of about 425° to about 600° C., preferably about 475° to about 550° C.

The alloy composition, the amount of final cold work and the processing during final thermal treatment may be adjusted to provide the desired phase at body temperature. Generally, the $A_f$ decreases as the temperature of the thermal treatment increases to a minimum at about 550° C. and then the $A_f$ increases as the temperature increases to the temperature of recrystallization which is over 600° C. Compositionally, the $A_f$ will increase with nickel above equiatomic amounts (50% of Ni and 50% Ti) and corresponding decreased amounts of titanium and alloying elements, and it will decrease with decreased amounts of nickel and increased amounts of other alloying components. While the compositional changes will change the values of $A_f$ they will not change the general relationship between $A_f$ and heat treatment temperature. A presently preferred composition for shape memory effects is 50.02% Ni and 49.98% Ti, and a presently preferred composition for stress induced pseudoelastic properties is 50.8% Ni and 49.2% Ti. Increasing amounts of cold work generally decrease both the martensitic and austenitic transformation temperatures, the latter to a lesser extent than the former.

In one preferred embodiment of the invention, the housing is a tubular member in a cold worked condition with one or more sections thereof heat treated to relieve stress. The heat treated sections develop increased overall housing flexibility which facilitates the advancement of the housing through tortuous passageways but the cold worked sections maintain the diametrical rigidity which maintains the circularity or other transverse cross-sectional shape of the internal housing chamber. In this embodiment, the sections which have been heat treated are in the martensite phase at body temperature and usually have an $A_f$ well above body temperature.

In another preferred embodiment of the invention, the housing is cold worked in the manner previously discussed and then the entire housing or a significant portion of the housing along its length is heated at a temperature above the $A_f$ minimum transformation temperature which will transform any martensite phase, which is relatively soft, to the austenite phase, which is relatively hard, while the housing is straight or in another desired configuration to generate the shape remembered. As used herein the austenite transformation temperature refers to a temperature at which martensite phase transforms to austenite upon the application of heat. This temperature may range from the temperature at which the transformation is initiated, identified as $A_s$, to the temperature at which the transformation is completed, identified as $A_f$. At. the midpoint temperature, $A_{50} = Af/2$, a substantial portion of the martensite present in the alloy has been transformed to the austenite. The $A_{50}$ is convenient to use because it is easily determined experimentally by DSC, which demonstrates a sharp reduction in the heat flow at the $A_{50}$. When the housing cools after the heat treatment the austenite phase will transform to the martensite phase which is stable at the lower temperature. In this case, should the housing become deformed within the patient's body, e.g. when advancing the housing through a patient's tortuous vasculature, the housing can be heated to a temperature above the $A_f$ temperature of the alloy of the housing to cause the martensite phase in the housing to transform to the austenite phase. The housing will transform to the configuration, e.g. straight condition or other desired configuration, which the austenite phase remembers. Upon cooling the housing to body temperature after the transformation, the austenite phase reverts to the martensite phase but the housing remains in the straight or other desired configuration which the austenite phase remembered. A variety of heating means may be employed to heat the martensite phase to a temperature above the $A_f$. For example, resistive or inductive heating, RF or microwave heating or conductive heating as with a heated fluid may be used.

When the housing of the invention is employed in an atherectomy catheter, it has been found convenient to rely upon the frictional engagement of the cutting blade with the interior of the housing while the cutter is rotated within the housing chamber at a relatively high rate of speed (e.g. 2000 rpm) to raise the temperature of the housing sufficiently above the $A$, transformation temperature so that the housing, if deformed, will revert to the straight or other memory of the austenite phase.

In yet another embodiment of the invention, the composition and thermomechanical processing are selected so that the housing is in the austenite phase at operating temperature, e.g. body temperature, and has pseudoelastic characteristics at that temperature, i.e. exhibits a stress-induced austenite to martensite transformation which occurs over a relatively constant stress level. During the initial application of stress to a housing in the austenite phase, the strain is for the most part proportional to the applied stress in a conventional manner. However, when the housing strain reaches about 2%, the stable austenite phase begins a stress-induced transformation to the martensite phase which is unstable at the operating temperature but which is stable as long as stress is applied at the appropriate levels. At a strain above about 2% the stress no longer increases but remains at a relatively constant plateau during the stress induced phase transformation to martensite while the strain continues to increase to about 8%. At a strain of about 8%, the stress-induced transformation of the austenite phase to the martensite phase is essentially complete. As the strain increases beyond about 8%, the strain again begins to rise in proportion to the applied stress. At a strain from about 8% to about 15% the deformation of the martensite is elastic, but at a strain above about 15% the deformation of the martensite becomes plastic or permanent. The stress-induced martensite is unstable at the operating temperature, so when the applied stress is lowered, the strain is reduced to a region with a second plateau of relatively constant stress, lower than the first plateau of relatively constant stress, where the stress-induced unstable martensite phase transforms back to the more stable austenite phase. If no permanent or plastic deformation has occurred to the housing, it will return to its initial shape when all the applied stress is removed. The housing of this embodiment preferably has an $A_f$ temperature less than body temperature to facilitate intracorporeal use. An example of the application of stress which would transform the austenite phase to the martensite phase might be when a housing having pseudoelastic properties passes through tortuous arterial passageways or through the tight curvature of the shaped distal end of a guiding catheter. The stresses on the housing causes the austenite phase to transform to the martensite phase, thereby allowing the housing to flex at relatively low and constant stress levels. However, when the stress is removed, the martensite phase reverts back to the stronger austenite phase which "remembers" its original shape or configuration which in this instance is preferably a straight condition.

These and other advantages of the invention will become more apparent from the following detailed description of the invention when taken in conjunction with the accompanying exemplary drawings.

BRIEF DESCRIPTION OF THE DRAWINGS

FIG. 1 is an elevational schematic view of an atherectomy catheter embodying features of the invention.

FIG. 2 is an enlarged longitudinal cross-sectional view of the distal end of the catheter shown in FIG. 1.

FIG. 3 is a transverse cross-sectional view of the catheter shown in FIG. 1 taken along the lines 3—3.

FIG. 4 is a perspective view of cutter housing suitable for use in the catheter shown in FIG. 1 which has heat treated flexible cylindrical sections of the housing.

FIG. 5 is a transverse cross-sectional view of the cutter housing shown in FIG. 4 illustrating the relative dimensions of the opening or window for receiving tissue to be removed.

FIGS. 6, 7, 8, 9, and 10 are elevational and plan views of alternative housings.

DETAILED DESCRIPTION OF THE INVENTION

Figure 11:
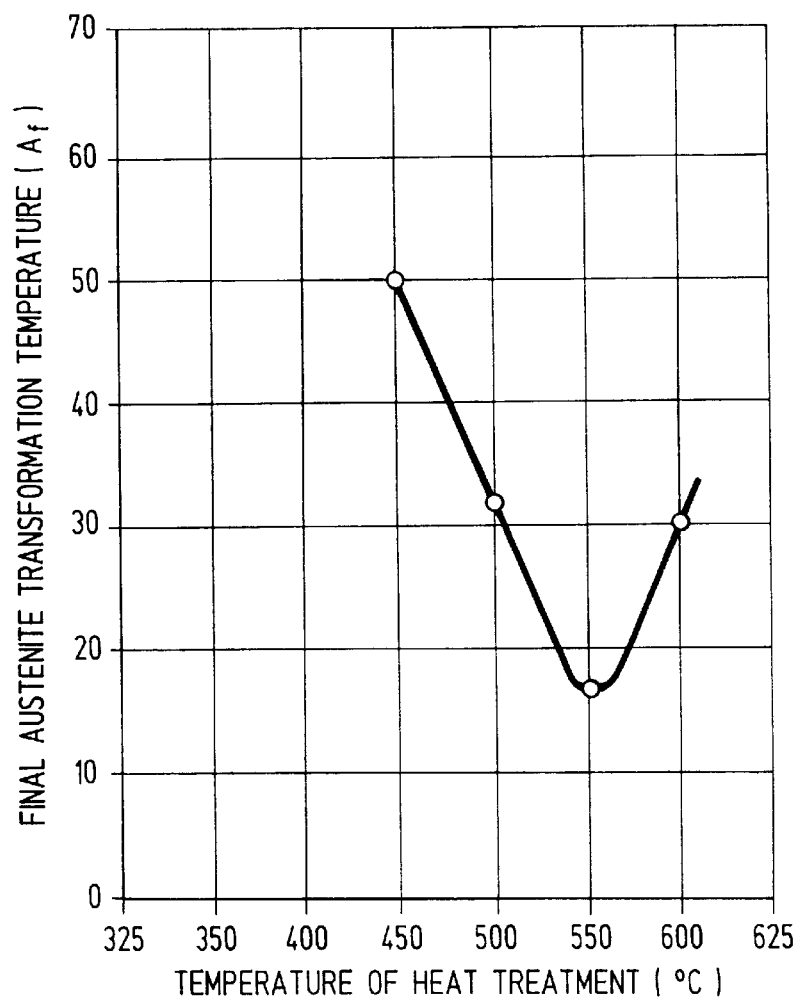
FIG. 11 is a graphical representation of the relationship between the final austenite transition temperature and the temperature of the thermal treatment given to a pseudoelastic NiTi alloy after cold working.

FIGS. 1–3 schematically depict an atherectomy catheter 10 embodying features of the invention. The catheter 10 includes a distal portion 11 having cutter head assembly 12, an elongated catheter shaft 13 and a proximal portion 14 having a manifold assembly 15 and drive assembly 16 (shown in phantom).

As shown in more detail in FIG. 2, the cutter head assembly 12 has a cylindrical housing 17 formed of shape memory/pseudoelastic alloy with a side opening or window 18 and a cutting blade 19 which is slidably disposed within the inner chamber 20 of the housing 17 for both longitudinal and rotational movement. The cutting blade 19 movement, both longitudinal and rotational is effected by the flexible cable drive shaft 21 which is secured to the proximal end of the cutter blade.

Inflatable positioning balloon 22 is secured to the exterior of the housing 17 on a side opposite to the window 18 so that, upon its inflation within the stenotic region of the patient's artery, the housing will be pressed against the stenotic material to cause some of it to enter into the inner chamber 20 where the cutter blade 19 can sever it from the rest of the stenotic material on the arterial wall. An inflation tube 23 is disposed within the outer tubular member 25 of the catheter shaft 13 and has a distal end spliced together with the proximal skirt 26 of the inflatable positioning balloon 22 to direct inflation fluid to the interior of the balloon. The distal skirt 27 of the balloon 22 is folded over and secured within the distal end of the housing as shown in FIG. 2. A torquing cable 28, which is also disposed within the outer tubular member 25, is secured to the proximal end of the housing 17 and is provided with a rotator 29 fixed by its distal end to the proximal end of the torquing cable to rotate the cutter head assembly 12 so that cutter head assembly may be initially positioned or repositioned within the patient's artery during the atherectomy procedure. The proximal end of the rotator 29 is rotatably secured to the manifold assembly 15 so that the torquing cable 28 can be rotated by rotation of the rotator 29 without moving the manifold assembly.

Flexible nose cone 30, which has an inner coil 31 and outer jacket 32, is secured to the distal end of the housing 17 to prevent traumatic engagement with the artery wall when the catheter 10 is advanced through the patient's arteries.

The triple arm manifold assembly 15 on the proximal portion 14 of the catheter 10 generally includes a manifold body 33 and inflation arm 34 and a flush arm 35. The inflation arm 34 is in fluid communication with the inner lumen of the inflation tube 23 for delivery of inflation fluid to the interior of the balloon 22. The flush arm 35 is in fluid communication with the interior of the flexible drive shaft 21 for the cutter blade 19 and is adapted to direct irrigation or radiopaque liquid to the interior of the housing 17.

The drive assembly 16 is interconnected to the drive shaft 21 for the cutter blade 19 by means of a splined connector 36 which is adapted to be inserted into the drive spline (not shown) of the drive assembly. The splined connector in turn is connected to an intermediate drive shaft 37 which is fixed in a driving relationship to the proximal end of the flexible drive shaft 21. A finger actuated lever 38 is rotatably mounted onto the intermediate drive shaft 37 but is fixed thereto to prevent longitudinal movement relative to the intermediate drive shaft so that longitudinal movement of the finger actuated lever will cause the longitudinal movement of the cutter blade 19 within the housing 17. The operation of the drive assembly 16 is initiated by the actuation of switch 39 which will cause the rotation of the flexible drive shaft 21 and the cutter blade 19 secured thereto. Further details of the drive assembly 16 can be found in U.S. Pat. No. 4,771,774 which has been incorporated herein by reference. The drive assembly and atherectomy catheter of the structure described herein with a conventional cutter housing formed of stainless steel are available from the assignee of the present application Devices for Vascular Intervention, Inc. (DVI), located in Redwood City, Calif.

FIGS. 4 and 5 illustrate the flexible housing 17 of the present invention which has a plurality of heat treated cylindrically shaped tubular sections 40 to provide improved housing flexibility. In one embodiment the housing 17 is formed of a shape memory alloy of nickel and titanium and typically is 50% Ni and 50% Ti. The entire housing 17 is initially in a cold worked condition by drawing through a series of dies of decreasing diameters, with intermediate anneals between working steps. The cylindrically shaped tubular sections 40 with a length of about 0.01 to about 0.2 inch (0.254–5.1 mm) are heat treated, preferably with a laser beam (e.g. $CO_2$ or YAG laser) with a spot size of about 0.002 to about 0.010 inch (0.051–0.254 mm) in diameter to stress relieve or otherwise heat treat the cylindrically shaped sections. The power output of the $CO_2$ laser is about 1 to about 7 watts. It is difficult to determine the temperature at which the laser treated tubular sections are subjected, so it may be necessary to go through a trial and error procedure to optimize the laser treatment for a particular housing wall thickness, housing composition and thermomechanical processing.

The size of the opening or window 18 in a wall portion of the housing 17 may vary. Generally, the cutout angle, shown best in FIG. 5, should range from about 80° to about 140°, and preferably about 90° to about 130°. It is contemplated that the atherectomy catheters will be offered with windows of various lengths to accommodate different sized stenoses.

FIG. 6 depicts an alternative cutter housing 17 wherein tubular section 41, which is more flexible than adjacent tubular sections 42 and 43, extends longitudinally across the window 18.

FIGS. 7 and 8 illustrate another embodiment of the invention wherein the housing 17 is provided with an elongated strip 50 in the martensite phase which is transformable to an austenite phase with a straight memory by the application of heat to raise the temperature of the strip to above the $A_f$ temperature. The rest of the housing is in a cold worked state.

FIGS. 9 and 10 illustrate yet another embodiment of the invention where the area 60 surrounding the opening 18 of the housing 17 is heat treated above the $A_f$, which preferably is above body temperature, to develop an austenite phase with a straight memory. Should the housing become deformed during use, it may be heated above the $A_f$ to cause the formation of the austenite phase which returns to the shape remembered, which in this case is straight.

In FIGS. 4 and 6–10 the area immediately adjacent to the area which has been heat treated may have properties intermediate the cold worked and heat treated properties thereby providing additional variations in properties which may be found helpful in designing a housing with multiple locations with various properties.

FIG. 11 is a graphical representation of the relationship between the $A_f$ of a NiTi alloy and the temperature at which the alloy is subjected to after cold working in the thermomechanical processing described herein. As shown, the $A_f$ decreases as the temperature of thermal treatment increases to a temperature of about 550° C. Thereafter, the $A_f$ increases until the temperature rises to the recrystallization temperature of the alloy. As previously indicated, the general shape of the graphical representation of the relationship remains essentially the same even though the composition of the alloy and the amount of cold work varies.

Figure 12:
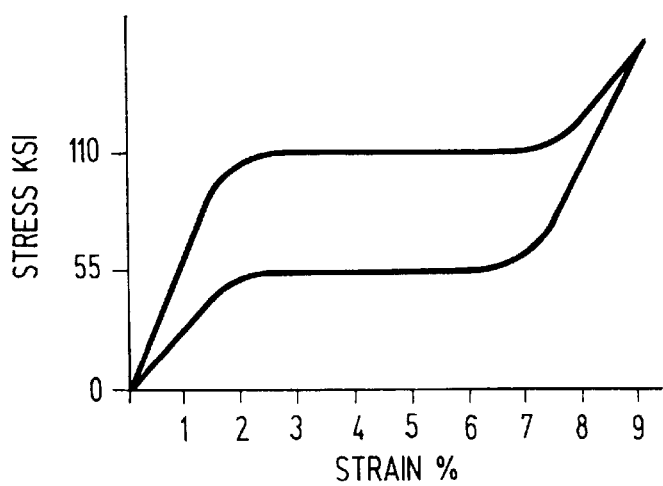
FIG. 12 is a graphical representation of the stress-strain relationship of a pseudoelastic NiTi alloy.

FIG. 12 is a graphical representation of the stress-strain relationship of a pseudoelastic NiTi alloy. As indicated the strain is proportional to stress up to a strain of about 2%. At about 2% strain the austenite phase begins to transform to martensite and continues the transformation to completion over a constant stress region to a strain of about 5%. Beyond a strain of about 8% the deformation is elastic to about 15% when it becomes plastic. Upon reduction of the stress level the material first returns to a constant stress plateau where the martensite phase transforms back to the austenite. Upon completion of the transformation at about a 2% strain the strain returns to zero if no permanent deformation has occurred.

An atherectomy catheter or other intracorporeal catheter with a flexible housing in accordance with the invention may be used in essentially the same manner of prior catheters, except for the notable difference that the characteristics of the housing can be changed within the patient's body by changing the temperature of the housing therein. If the housing is in the martensite phase at body temperature and the housing has been provided with a desired "remembered shape" at an austenite transformation temperature above body temperature, the housing may be heated within the body to a temperature at or above the $A_{50}$ of the shape memory alloy so that the housing will transform to essentially the shape remembered. If the housing is in the austenite phase at body temperature and it is desired to transform the austenite phase to the lower strength martensite, e.g. when it is desired to have a more flexible housing such as when moving the housing through tortuous passageways, the temperature of the housing can be reduced to a temperature at or less than the $M_{50}$ of the shape memory alloy. By allowing the housing to return to body temperature, the martensite transforms back to austenite and the shape of the housing returns to the remembered shape suitable for the procedure, e.g. straight.

The temperature of the housing can be changed when the catheter is within the patient's body by a variety of suitable means. For example, the temperature of the housing can be raised by resistance/inductance heating with electrical conductors in contact with or formed integral with the housing. One convenient method of heating the housing with atherectomy catheters which have cutting elements within the housing which fictionally engage the housing is to move the cutting element within the inner chamber with sufficient velocity to raise the temperature of the housing to the desired level above body temperature. Other means of heating the housing within the patient's body include directing a fluid at elevated temperature through an inner lumen of the catheter which is in fluid communication with the interior of the housing. RF heating may also be employed as will be recognized by those skilled in the art. If it is desired to lower the temperature of the housing, a fluid at a temperature less than body temperature may be directed through an inner lumen within the catheter to the interior of the housing.

While the housing of the present invention has been described herein in terms of certain presently preferred embodiments directed to atherectomy catheters, those skilled in the art will recognize that it may be used in a wide variety of intracorporeal devices for performing diagnostic or therapeutic procedures within a patient's body lumen or body cavity. Various modifications and improvements can also be made to the invention without departing from the scope thereof.

What is claimed is:

1. A method of making a flexible hollow housing for intracorporeal use comprising:
   a) forming a cold worked hollow body of shape memory alloy for intracorporeal use, having an interior chamber extending therein; and
   b) heat treating a plurality of tubular sections of the cold worked hollow body to stress relieve the cold worked material in the tubular sections and to develop a martensite phase which is stable at body temperature and which has a martensite to austenite transition temperature above body temperature and leaving an untreated cold worked tubular section of the hollow body disposed between at least two heat treated tubular sections.

2. The method of claim 1 wherein the heat treated sections have a straight memory in an austenite phase.

3. A method of making a flexible hollow housing for intracorporeal use comprising:

a) forming a cold worked hollow body of shape memory alloy for intracorporeal use, having an interior chamber extending therein, a wall portion, and an opening in the wall portion; and b) heat treating an integral portion of the cold worked hollow body defining at least in part the opening to stress relieve the cold worked material in the integral portion and to develop a martensite phase which has a martensite to austenite transition temperature below body temperature, and leaving a significant portion of the hollow body as nonheat treated material in the cold worked state in a surrounding relation to the heat treated portion, wherein the heat treated portion of the hollow body exists in a stable austenite phase at body temperature and has a reversible martensitic phase transformation in response to stress.

4. The method of claim 3 wherein the heat treated portion extends in a linear fashion parallel to the longitudinal axis of the hollow body along the length of the hollow body.

5. The method of claim 4 wherein the austenite phase has a straight memory.

6. The method of claim 3 wherein the heat treated portion is a plurality of rings along the length of the hollow body being concentric to and longitudinally adjacent to the non-heat treated material of the hollow body, and being separated from one another along the length of the hollow body by sections of the nonheat treated material which are longer than the heat treated rings.

7. The method of claim 3 wherein the heat treated portion is laterally adjacent to nonheat treated material of the hollow body.

* * * * *